United States Patent
Anderson

(10) Patent No.: US 6,209,384 B1
(45) Date of Patent: Apr. 3, 2001

(54) SOLENOID OPERATED MOLTEN METAL PROBE

(76) Inventor: Daniel A. Anderson, 5 Scenery Hill Dr., Greensburg, PA (US) 15601

(*) Notice: Subject to any disclaimer, the term of this patent is extended or adjusted under 35 U.S.C. 154(b) by 0 days.

(21) Appl. No.: 09/243,562

(22) Filed: Feb. 3, 1999

(51) Int. Cl.[7] .................................................. G01N 33/20
(52) U.S. Cl. ............................................. 73/19.07; 702/24
(58) Field of Search ................................ 73/19.07, 19.01, 73/864.34, 864.73, 864.81; 436/75; 148/508; 702/24

(56) References Cited

U.S. PATENT DOCUMENTS

| | | | |
|---|---|---|---|
| 4,731,732 | * | 3/1988 | Warchol et al. ........................ 702/24 |
| 5,495,746 | * | 3/1996 | Sigworth ............................. 73/19.07 |
| 5,591,894 | * | 1/1997 | Falk et al. ............................ 73/19.07 |
| 5,850,034 | * | 12/1998 | Hugens, Jr. ........................... 73/19.07 |

\* cited by examiner

*Primary Examiner*—Hezron Williams
*Assistant Examiner*—Jay L. Politzer
(74) *Attorney, Agent, or Firm*—Jones, Tullar & Cooper, P.C.; Daniel A. Sullivan, Jr.

(57) ABSTRACT

Apparatus for determining gas content in a liquid metal. The apparatus includes a hollow tubular probe having one end for disposal in the liquid metal, and the other end connected to a housing containing a gas sensing element. A hollow piston is located in the hollow probe for disposal in the liquid metal through the end of the probe disposed in the liquid metal, the piston having a lower porous end. A solenoid coil having a plunger translatable in the coil is connected to means mechanically connecting the plunger to the piston for vertically moving the piston in the liquid metal.

13 Claims, 2 Drawing Sheets

SOLENOID OPERATED MOLTEN METAL PROBE

BACKGROUND OF THE INVENTION

Figure 1:
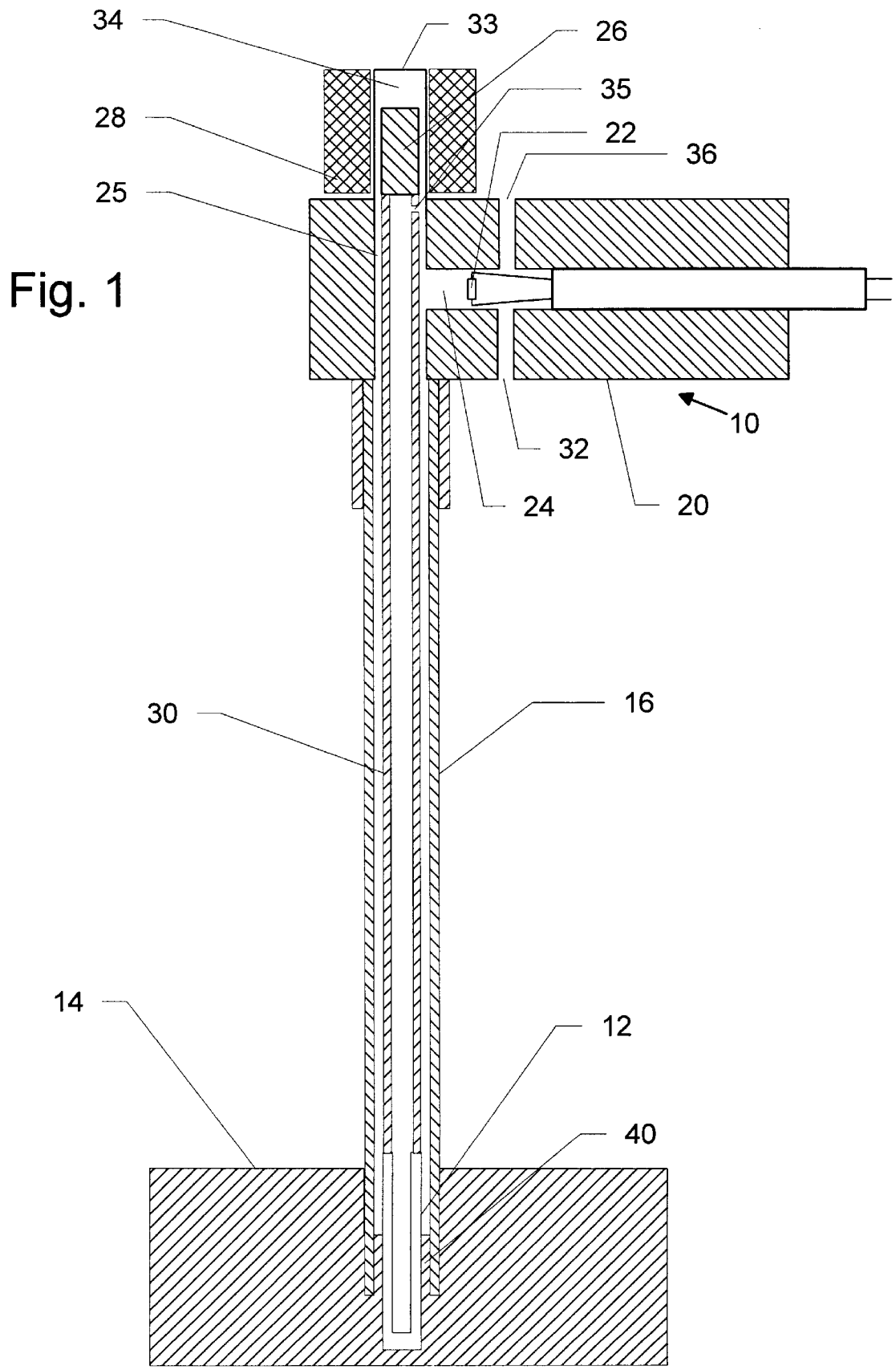

The present invention relates generally to probes used in collecting and sensing the gas content of liquid, molten metal, and more particularly to a hollow probe providing efficient collection of gas contained in a liquid metal.

It is known that hydrogen dissolved in molten metal, such as aluminum and aluminum alloys, causes voids or pores to develop within an ingot cast from such molten metal, the voids forming during the process of solidification. The voids give rise to various problems in products produced from the solidified metal. There has, therefore, been increasing requirements that a so-called dehydrogenation process be performed, i.e., that hydrogen dissolved in molten metal be removed as an important step in metal casting processes.

Before any removal of hydrogen gas takes place, of course, it is necessary to determine whether or not a body or supply of molten metal contains sufficient amounts of hydrogen for the removal process. This determination can be made by hydrogen sensing apparatus, such as those disclosed in the following U.S. Pat. Nos.:

2,861,450—Ransley
4,454,748—Warchol et al
4,731,732—Terai et al
4,829,810—Anderson et al
4,907,440—Martin et al The disclosures of these patents are incorporated herein by reference.

In the above references, the content of hydrogen dissolved in a body of molten metal is determined by directing an inert carrier gas into the molten metal, and circulating the carrier gas a substantial number of times in the metal. In the process, the carrier gas acquires hydrogen gas from the molten metal when it is first brought in contact with such metal, and the acquired hydrogen content in the carrier gas increases in each period of contact until the hydrogen partial pressure in the carrier gas equilibrates with the hydrogen partial pressure in the metal.

Generally, the number of contacts required between the carrier gas and the liquid metal is relatively large before equilibrium is reached. A pump is used for this process to circulate the mixture of carrier gas and hydrogen content to and through a hydrogen sensing device and to and from the liquid metal.

Carrier gases are conducted into liquid metals and removed therefrom by hollow probe devices, such as shown in the above-incorporated patent references using pumps, tubing and check valves that control the direction of carrier gas to and from the liquid metal.

SUMMARY OF THE INVENTION

The present invention uses a simple, hollow, heat-resistant tube and probe having one end located in a body or supply of liquid metal, and a piston located in said end for reciprocation in the end of the probe and in the liquid metal. The piston is reciprocated in the tube and metal by a solenoid plunger, and the hollow tube and probe are connected in fluid communication with a hydrogen gas sensor. Gas is forced up the hollow tube from the liquid metal and reciprocating piston to the sensor by action of the reciprocating piston. The piston is mechanically connected to the solenoid plunger by a shaft located in the hollow probe, and the hollow probe can be connected directly to a sensor housing such that the number of connections and fittings, which can be subject to leakage, is kept to the one connection between the sensor housing and the hollow probe.

Cyclic movement of the piston in the end of the probe located in the liquid metal disturbs only the surface of the liquid metal disposed within the probe, i.e., the metal surface located outside of the probe remains undisturbed. Disturbance of the metal surface outside the probe causes hydrogenation of the liquid metal, as water vapor from the atmosphere above the liquid metal easily enters the liquid metal. This, of course, adversely influences the measurement of gas content, as the sensor must deal with extraneous sources of hydrogen.

The volume of the hollow probe is small such that the reciprocating piston rapidly fills the hollow probe with a mixture of hydrogen and carrier gas. There is no separate pump and no interconnecting tubing to be filled with carrier and hydrogen gases. Thus, the time for making the measurement is quite short, i.e., on the order of several minutes.

In addition, no check valves are needed, which valves can also be subject to leakage and require maintenance.

The solenoid can be operated by a cyclic voltage supplied by a source of electrical energy. The source, for example, can provide repetitive electrical pulses having a magnitude sufficient to energize the solenoid to respectively raise the piston, and using the absence of pulses, to lower the piston, i.e., the piston falls under the force of its own mass.

THE DRAWING

Figure 2:
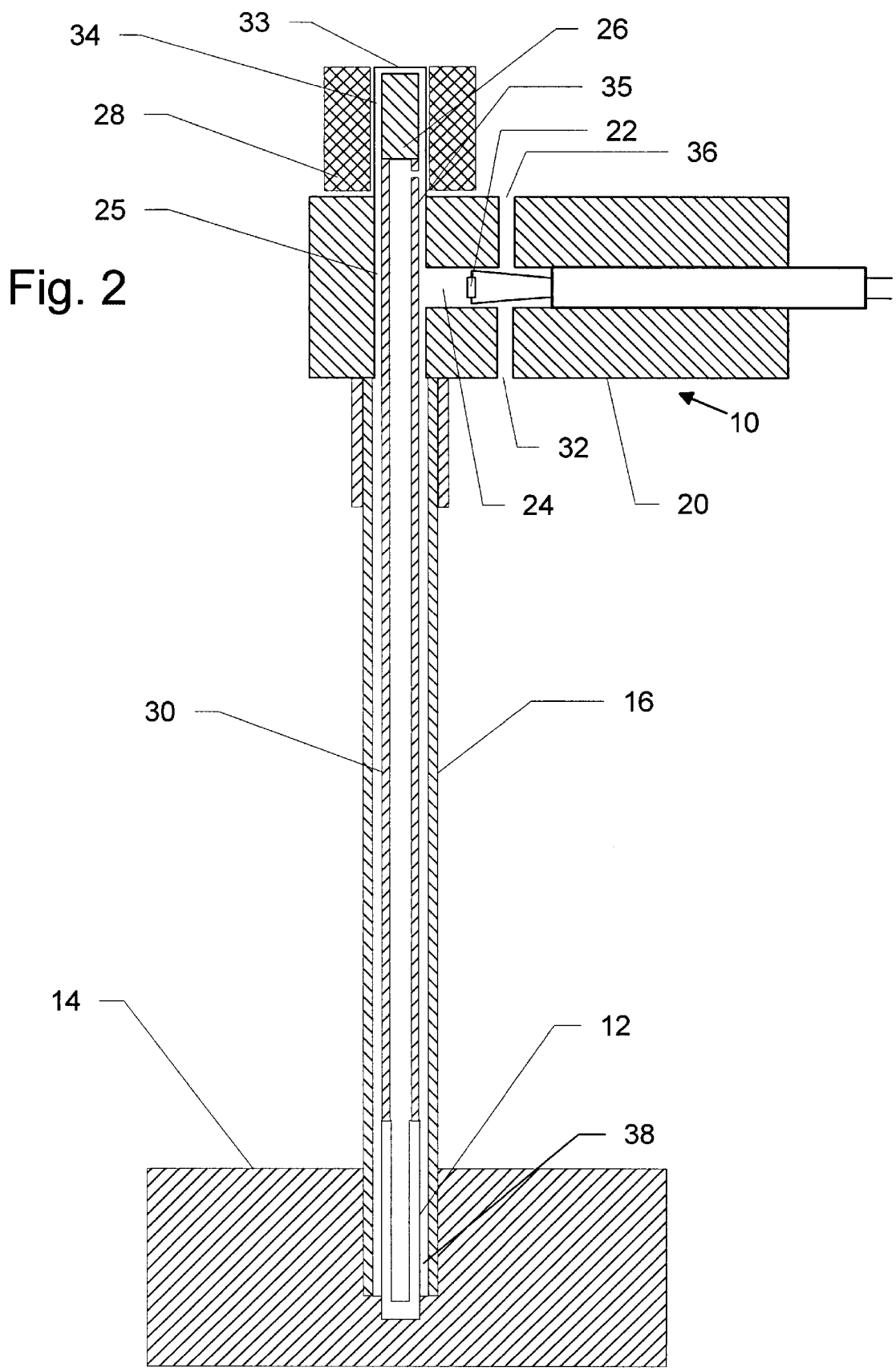

The invention, along with its advantages and objectives, will be better understood from consideration of the following detailed description and the accompanying drawing, in which:

FIG. 1 is a cross-sectional view of the apparatus of the invention in which a solenoid mechanically connected to a piston in a hollow probe is shown in a de-energized state, and FIG. 2 is the same sectional view of the apparatus except that the solenoid is shown in an energized state.

PREFERRED EMBODIMENT

Referring now to the drawing figures, an apparatus 10 is shown for cyclically moving a piston 12 in a body of liquid metal 14, such as a supply of molten aluminum and alloys thereof, though use of the invention is not limited to sensing gases in molten aluminum.

Piston 12 can have a solid sidewall and porous ends for receiving and dispensing gas located in the piston into the liquid metal beneath the piston and into a hollow tubular probe 16 extending upwardly from the piston to a housing block 20 containing a gas sensor 22, such as a hot wire or film sensor. Such a sensor is well known and is connected to associated known circuitry (not shown) employed in sensing hydrogen gas content in liquid metal.

Housing 20 can be made from a solid block of brass or aluminum (or other suitable material) and provided with a hollow portion or chamber 24 for accommodating sensor 22, and a hollow bore 25 for receiving a magnetically permeable plunger 26 of a solenoid coil 28 and the upper end of a shaft or stem 30 suitably connected to plunger 26.

Piston 12 can be made by covering the lower end of shaft 30 with a suitable heat resistant material, a preferred material being Nextel® which is a porous woven ceramic fiber material made by 3M. Nextel® is also a trademark owned by 3M. If the complete piston is made of Nextel®, it is entirely porous. The material of the piston can also be a suitable heat resistant porous ceramic material. A suitable material for stem 30 is porous alumina or silicon carbide.

A cap 33 is located in the hollow of solenoid coil 28 and above plunger 26. Cap 33 forms a chamber 34 containing the plunger and seals hollow bore 25 above shaft 30 while the portion of the shaft below housing block 20 is enclosed by hollow probe 16, which probe extends into liquid metal 14 to complete the seal of the probe.

In the figures, shaft 30 is depicted as a hollow stem that opens to hollow portion 25 of block 20 and chamber 34 via a lateral port 35. This port places the shaft in fluid communication with bore 25 and with chamber 24 that houses sensor 22.

Operation of apparatus 10 is as follows. The lower ends of probe 16 and piston 12 are inserted into liquid metal 14, and a carrier gas is supplied under pressure to sensor chamber 24 via a port 32 provided in block 20. The carrier gas can, for example, be supplied to port 32 from a cylinder of the gas (not shown), the gas being held in the cylinder under an appropriate pressure.

After arriving in chamber 24, the carrier gas flows from the chamber to chamber 34 via bore 25 and to and through the hollow probe 16 to the liquid metal 14. A small amount of carrier gas can also flow downwardly through stem 30, if hollow, and into piston 12 and into the liquid metal through the piston. The measurement is initialized by admitting carrier gas to purge the apparatus of oxygen.

When solenoid coil 28 is energized to raise plunger 26, as shown in FIG. 2, carrier gas is forced out of chamber 34 and downwardly through probe 16 and around and through hollow piston 12 into liquid metal 14. The gas flowing downwardly forces an amount of liquid metal out of the end of hollow probe 16, as indicated by numeral 38 in FIG. 2, equal to the gas displaced by plunger 26 in chamber 34. The carrier gas entering the liquid metal contacts and acquires hydrogen gas contained in the liquid metal to form a mixture of carrier and hydrogen gas. Gas located in the liquid metal beneath the porous end of the piston enters the piston through the porous end and into the hollow stem 30, and into hollow probe 16 from the liquid metal located about the piston.

The raised position of plunger 26 and piston 12 in FIG. 2 is one half or one portion of a cyclic motion of the plunger and piston effected by energization of solenoid 28. Between each occurrence of energization, the plunger and piston fall under the force of gravity.

When the plunger moves downwardly in the cycle, chamber 34 is evacuated by plunger 26 which pulls the carrier and hydrogen gas mixture up hollow probe 16 until the pressure chamber in chamber 34 is equal to that in the lower end of probe 16. Simultaneously the metal level in the lower end of probe 16 fills with an amount of metal 40 (FIG. 1) equal to the volume of gas displaced from the area 38 in FIG. 2. Hydrogen gas diffuses evenly throughout the carrier gas including the volume in chamber 24 occupied by sensor 22. Sensor 22 produces an electrical output which is proportional to the partial pressure of hydrogen in the gas mixture. Gas can flow up the center of stem 30 to the sensor if the stem is hollow. A port 36 in block 20 allows the sensor chamber to be purged (zeroed) with carrier gas between readings without ejecting gas out the bottom of probe 16, and without purging the probe. Only the sensor chamber need be purged. The purging of additional volumes, as in prior art, is unnecessary and wastes time The cyclic motion of the piston 12 and plunger 26 is continued until the partial pressure of hydrogen in the carrier gas mixture equilibrates with the pressure of hydrogen inside the liquid metal. The procedure usually takes several minutes, typically less than 10 minutes.

Because the motion of piston 12 is contained inside hollow probe 16, the surface of the liquid metal outside of the probe is not disturbed by motion of the piston 12. It is well established that disturbing the surface of liquid metal, particularly liquid aluminum, enhances the adsorption of atmospheric gases, particularly water vapor. This adsorption of atmospheric gases can distort the measurement by introducing extraneous gases into the hydrogen/carrier gas mixture inside hollow probe 16. In addition, the motion of the piston 12 inside the liquid metal enhances transfer of hydrogen into the carrier gas from the liquid metal, thereby effecting a more rapid measurement. Further, because there is no separate pump and associated connecting tubes, the volume of the instrument is minimized. This also enhances the speed of the measurement because less hydrogen needs to be removed from the liquid metal before the partial pressure of hydrogen equilibrates in the carrier gas.

Hollow probe 16 is a simple tube. It can be made of a suitable ceramic material such as alumina or silicon nitride, but it may also be made of metal, such as carbon steel, provided the metal does not dissolve quickly in the liquid metal being analyzed. Metal used for hollow probe 16 can be coated to prolong its life in the liquid metal being analyzed. It is preferable that the coating be smooth and non-porous because porous coatings allow communication of atmospheric gases along the coated portion of the probe and thence into the carrier gas mixture. The design of probe 16 is particularly suitable to be resistant to liquid metal because it can be made massive enough to last considerable time before dissolving in the liquid metal being analyzed. Other probe designs rely on small diameter tubing which quickly dissolves in liquid metal and, therefor, must be coated with a porous thermal shock resistant coating to achieve acceptable life. (Coating porosity provides resistance to shock.)

What is claimed is:

1. Apparatus for determining gas content in a liquid metal, the apparatus comprising:
    a hollow tubular probe adapted to contain a carrier gas, having one end for disposal in the liquid metal, and the other end connected to a housing containing a gas sensing element,
    A piston located in said hollow probe for disposal in said liquid metal through the end of the probe disposed in the liquid metal, said piston having a lower porous end,
    solenoid coil having a plunger translatable in the solenoid, and
    means mechanically connecting said plunger to the piston for vertically reciprocating said piston in the liquid metal.

2. The apparatus of claim 1 wherein the piston is hollow.

3. The apparatus of claim 1 wherein the means mechanically connecting the plunger to the piston is a stem of shaft extending through the hollow probe.

4. The apparatus of claim 1 wherein the solenoid includes a coil located outside of the housing containing the sensing element.

5. The apparatus of claim 1 wherein the gas content in the liquid metal is hydrogen, and the sensing element is a hydrogen gas sensing element.

6. The apparatus of claim 1 wherein the probe is made of a heat resistant material suitable for immersion in molten metal.

7. The apparatus of claim 1 wherein the piston is made of a porous ceramic material.

8. The apparatus of claim 1 wherein the piston is made of Nextel®.

9. The apparatus of claim 1 wherein the end of the piston for disposal in the liquid metal is a Nextel® sleeve located on secured to the end of the stem or shaft.

10. A method of sensing the amount of gas content in a body of liquid metal, comprising:

disposing one end of a tubular probe containing a porous piston in a body of liquid metal, cyclically moving the piston in the tubular probe and in the body of liquid metal, using the cyclic movement of said piston to rapidly saturate a carrier gas in the probe with the gas content in the liquid metal, contacting a sensor with the gas-content saturated carrier gas, and using said sensor to determine the amount of gas content in the body of liquid metal.

11. The method of claim 10 including:

using upward movement in the cyclic motion of the piston in the probe and in the liquid metal to force gas in the piston downwardly through the piston and into the liquid metal, and to force gas in the liquid metal beneath the piston into the piston and upwardly into the probe and into a housing containing the gas sensor and connected in fluid communication with the probe.

12. The method of claim 11 including:

using downward movement of the piston of the cyclic motion to force gas out of the sensor housing and into the probe and downwardly through the probe and piston, and upwardly through the probe to a solenoid chamber connected in fluid communication with the housing containing the sensor.

13. The method of claim 12 including:

using a solenoid coil and plunger to provide the cyclic movement of the piston, and cyclically moving said plunger into and from the solenoid chamber.

\* \* \* \* \*